United States Patent [19]
Bedwell

[11] Patent Number: 5,840,702
[45] Date of Patent: Nov. 24, 1998

[54] CYSTIC FIBROSIS TREATMENT

[75] Inventor: David M. Bedwell, Birmingham, Ala.

[73] Assignee: UAB Research Foundation, Birmingham, Ala.

[21] Appl. No.: 620,866

[22] Filed: Mar. 22, 1996

[51] Int. Cl.$^6$ ....................................... A61K 31/70
[52] U.S. Cl. .................................. 514/23; 514/24; 514/25; 514/866
[58] Field of Search ................................. 514/23, 24, 25, 514/866

[56] References Cited

U.S. PATENT DOCUMENTS

| | | | |
|---|---|---|---|
| 5,384,128 | 1/1995 | Meezan et al. | 424/450 |
| 5,441,938 | 8/1995 | Speert et al. | 514/23 |

OTHER PUBLICATIONS

Chemical Abstracts (107:228540) 1997. Oliver et al.

*Primary Examiner*—Kevin E. Weddington
*Attorney, Agent, or Firm*—Benjamin Aaron Adler

[57] ABSTRACT

The present invention provides a method of stimulating expression of a functional full-length cystic fibrosis transmembrane conductance regulator protein in an individual in need of such treatment, comprising the step of administering to said individual a pharmacologically effective dose of an aminoglycoside. Also provided is a method of treating cystic fibrosis in an individual in need of such treatment, comprising the step of administering to said individual a therapeutically effective dose of an aminoglycoside. Further provided is a method of screening for a drug useful in the treatment of an individual having cystic fibrosis, comprising the step of determining said drug's ability to suppress premature stop mutations in a model of cystic fibrosis and a method of pharmacologically suppressing premature stop mutations in an individual having such mutations, comprising the step of administering to said individual a pharmacologically effective dose of an aminoglycoside.

12 Claims, 10 Drawing Sheets

CYSTIC FIBROSIS TREATMENT

FEDERAL FUNDING LEGEND

This invention was created using funds from the U.S. government under grant NIH DK 50832. Consequently, the federal government has certain rights in this invention.

BACKGROUND OF THE INVENTION

1. Field of the Invention

The present invention relates generally to the fields of molecular genetics and pharmacotherapy of genetic diseases. More specifically, the present invention relates to a novel treatment for cystic fibrosis using aminoglycoside antibiotics.

2. Description of the Related Art

The triplet genetic code is used by both prokaryotic and eukaryotic organisms to determine the sequence of amino acids incorporated during protein synthesis. The use of a specific set of codons to specify the incorporation of each amino acid is highly conserved among most organisms. In keeping with this conservation, translation is almost always initiated at a methionine (AUG) codon, while the end of translation is signaled by either an amber (UAG), ochre (UAA), or opal (UGA) termination codon. Knowledge of most aspects of protein synthesis has increased significantly over the last three decades. However, the details of translation termination have generally lagged behind an understanding of other steps of the translation process. Translation termination is initiated when a termination codon enters the ribosomal A site (FIG. 1). Polypeptide chain release factor recognizes the termination signal and facilitates the release of the completed polypeptide chain from the peptidyl-tRNA in a process that is normally very efficient. However, under certain conditions polypeptide chain release can be suppressed by one of two mechanisms. Suppression can occur by the direct misincorporation of an amino acid at the termination codon, leading to continued translation in the original reading frame. Alternatively, termination can be suppressed by ribosomal frameshifting, which results in continued translation in a new reading frame.

The process of translation termination has been studied most extensively in *E. coli*. One of the major factors found to effect the efficiency of translation termination (or conversely, the rate of termination suppression) in *E. coli* is the local sequence context surrounding the termination codon. The upstream sequence context has been shown to affect the efficiency of translation termination in only a limited number of cases (Feinstein and Altman, 1977; Buckingham et al., 1990; Moffat et al., 1994; Mottagui-Tabar et al., 1994), and a generally accepted model for the role of upstream sequences in this process has not yet emerged. In contrast, the importance of nucleotides distal to the termination codon has been more clearly established. Results from a large number of studies indicate that the nucleotide sequence immediately distal to the termination codon plays an important role in determining the efficiency of translation termination in this prokaryotic organism (Feinstein and Altman, 1977; Bossi and Roth, 1980; Engelberg-Kulka, 1981; Bossi, 1983; Miller and Albertini, 1983; Ayer and Yarus, 1986; Pedersen and Curran, 1991; Kopelowitz et al., 1992). Consistent with these results, the nucleotide context immediately following known termination codons in both prokaryotic and eukaryotic species is clearly non-random (Brown et al, 1990; Brown et al., 1993). This observation led to the proposal that polypeptide chain release factors may recognize a tetranucleotide (rather than a triplet) termination signal to facilitate polypeptide chain release. A recent analysis of the role of the first nucleotide distal to the termination codon supports the existence of an extended termination sequence in *E. coli* (Poole et al., 1995).

The importance of the local sequence context in determining the efficiency of translation termination in eukaryotic organisms is much less well characterized, and is derived largely from the study of naturally occurring examples of termination suppression in viral systems. For example, translation of the gag-pol reading frame in Maloney murine leukemia virus depends on the suppression of an in-frame amber termination codon, which normally occurs at a frequency of 5–10% (Yoshinaka et al., 1985). Suppression of translation termination in this system has been shown to be mediated by a distal sequence that includes an RNA pseudoknot (Wills et al., 1991; Feng et al., 1992). Furthermore, this mechanism of suppression does not appear to be codon specific, since ochre and opal codons are also suppressed by this sequence context (Feng et al., 1989; Feng et al., 1990). Because readthrough in this system requires a downstream pseudoknot structure, expression of the complete gag-pol reading frame appears to be an example of reprogrammed genetic decoding, or recoding (Gesteland et al., 1992). Recoding occurs when specific sequence elements (such as a pseudoknot) cause normally rare events such as readthrough or frameshifting to occur at a physiologically significant level. In another natural example of the suppression of translation termination, the expression of the RNA replicase of tobacco mosaic virus also depends on the readthrough of an in-frame amber codon (Pelham, 1978). A systematic study of this process in tobacco protoplasts concluded that upstream sequences did not play a significant role in mediating readthrough. However, a nucleotide sequence motif immediately distal to the termination codon having the consensus CARYYA was capable of reducing the efficiency of readthrough (Skuzeski et al., 1991). This distal sequence also reduced the termination efficiency at ochre and opal termination codons. More recently, Tate and co-workers found that the sequence context distal to the stop codon also plays a role in the efficiency of translation termination in human cells, particularly the first nucleotide following the stop codon (McCaughan et al, 1995).

The characterization of factors that facilitate the process of translation termination has lagged behind the analysis of other components of the translation machinery. This delay was caused in part by the incorrect identification of a tryptophanyl tRNA synthetase as the polypeptide chain release factor several years ago (Lee et al., 1990). This error was recently corrected, however, and the release factor has recently been suggested to consist of two components: a polypeptide involved in the recognition of the stop codon, termed eukaryotic Release Factor 1 (eRF1); and a second polypeptide, eukaryotic Release Factor 3 (eRF3), that contains a consensus GTP binding site (Timchenko and Caskey, 1994; Frolova et al., 1994; 1995). The eRF3protein acts to stimulate the activity of eRF1, and is called eRF3rather than eRF2 by virtue of its functional homology to RF3 of *E. coli*. However, essentially nothing is yet known about how these factors mediate the release of the completed polypeptide chain from the aminoacyl tRNA bound to the ribosomal P site in prokaryotes or eukaryotes.

Cystic fibrosis (CF) is caused by mutations in the gene encoding the CF transmembrane conductance regulator (CFTR). Over 400 distinct mutations in CFTR have been shown to cause CF. The most common of these mutations is the deletion of a phenylalanine at residue 508 (DF508), which is found on 70% of all CF chromosomes. However, severe CF is also caused by a number of different premature stop mutations, which are found on at least 5% of all CF chromosomes. Based upon this frequency, this class of mutations is more common than any single CF-causing mutation other than DF508. Thus, a strategy capable of correcting this entire class of mutations would have a major impact on the survival of a significant fraction of the CF patient population. Although this approach is not expected to restore CFTR function to wild type levels, recent studies have shown that even a small increase in CFTR expression in transgenic mouse models can lead to a significant decrease in the pathology associated with CF (Dorin et al., 1995). In more general terms, premature stop mutations have also been identified in a large number of other human diseases. A recent review catalogued 178 examples of human diseases that resulted from the introduction of premature stop mutations (Atkinson and Martin, 1994). This list included many common diseases such as cancer, diabetes, and hypercholesterolemia that strike a relatively large portion of the general population. As an example, over 25 distinct premature stop mutations that lead to cancer have been identified in the P53 gene alone. Thus, a strategy aimed at suppressing these mutations in CFTR could also be adapted to treat individuals with many other diseases that result from premature stop mutations.

The prior art is deficient in the lack of effective means of treating cystic fibrosis and other genetic diseases involving premature stop mutations. The present invention fulfills this longstanding need and desire in the art.

SUMMARY OF THE INVENTION

The present invention demonstrated that two common, disease-associated premature stop mutations in CFTR can be suppressed by aminoglycoside antibiotics, resulting in the expression of full-length, functional CFTR. Suppression occurred at relatively low, non-toxic levels of these drugs. The present invention indicates that a clinical strategy utilizing aminoglycoside treatment would restore CFTR function in CF patients with premature stop mutations.

It is an object of the present invention to demonstrate the ability of aminoglycoside antibiotics to suppress naturally-occurring premature stop mutations in model CFTR expression systems.

It is another object of the present invention to analyze aminoglycoside-based suppression of premature stop mutations in cells that express CFTR from the nuclear genome.

It is an object of the present invention to demonstrate that aminoglycoside-mediated suppression restores CFTR synthesis and function.

It is another object of the present invention to characterize the molecular mechanism of aminoglycoside-mediated suppression of premature stop mutations.

It is another object of the present invention to present the first clinical strategy aimed at overcoming a defect in decoding the genetic information encoded in a patient's genome that would restore the expression of an endogenous, functional protein.

Thus, in accordance with the above-mentioned objects, in one embodiment of the present invention, there is provided a method of stimulating expression of a functional full-length cystic fibrosis transmembrane conductance regulator protein in an individual in need of such treatment, comprising the step of administering to said individual a pharmacologically effective dose of an aminoglycoside.

In another embodiment of the present invention, there is provided a method of treating cystic fibrosis in an individual in need of such treatment, comprising the step of administering to said individual a therapeutically effective dose of an aminoglycoside.

In yet another embodiment of the present invention, there is provided a method of screening for a drug useful in the treatment of an individual having cystic fibrosis, comprising the step of determining said drug's ability to suppress premature stop mutations in a model of cystic fibrosis.

In still yet another embodiment of the present invention, there is provided a method of pharmacologically suppressing premature stop mutations in an individual having such mutations, comprising the step of administering to said individual a pharmacologically effective dose of an aminoglycoside, said aminoglycoside is selected from the group consisting of gentamicin, G418, hygromycin B, paromomycin, tobramycin and Lividomycin A.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the expression of full-length CFTR from the CFTR G542X and R553X cDNAs in the presence of G-418. HeLa cells infected with cTF7-3 at an MOI=10 and transfected using lipofectin (BRL) with wild type or mutant CFTR cDNAs were treated with G-418 for 8 hours. Cells were labeled with [$^{35}$S] methionine for 1 hour prior to cell lysis and CFTR was immunoprecipitated using a monoclonal antibody to the C-terminus (Genzyme). Proteins were resolved by SDS-PAGE and visualized by fluorography.

FIG. 3 shows the functional CFTR expression monitored as cAMP-induced anion efflux using the halide-sensitive fluorophore 6-methoxy-N-(3-sulphopropyl) quinolinium (SPQ).

FIG. 7 shows the effect of DIDS on whole-cell currents in IB3-1 cells treated with G-418. The holding potential was stepped in 20 mV increments from −100 mV to +100 mV at 800 ms intervals.

DETAILED DESCRIPTION OF THE INVENTION

Figure 1:
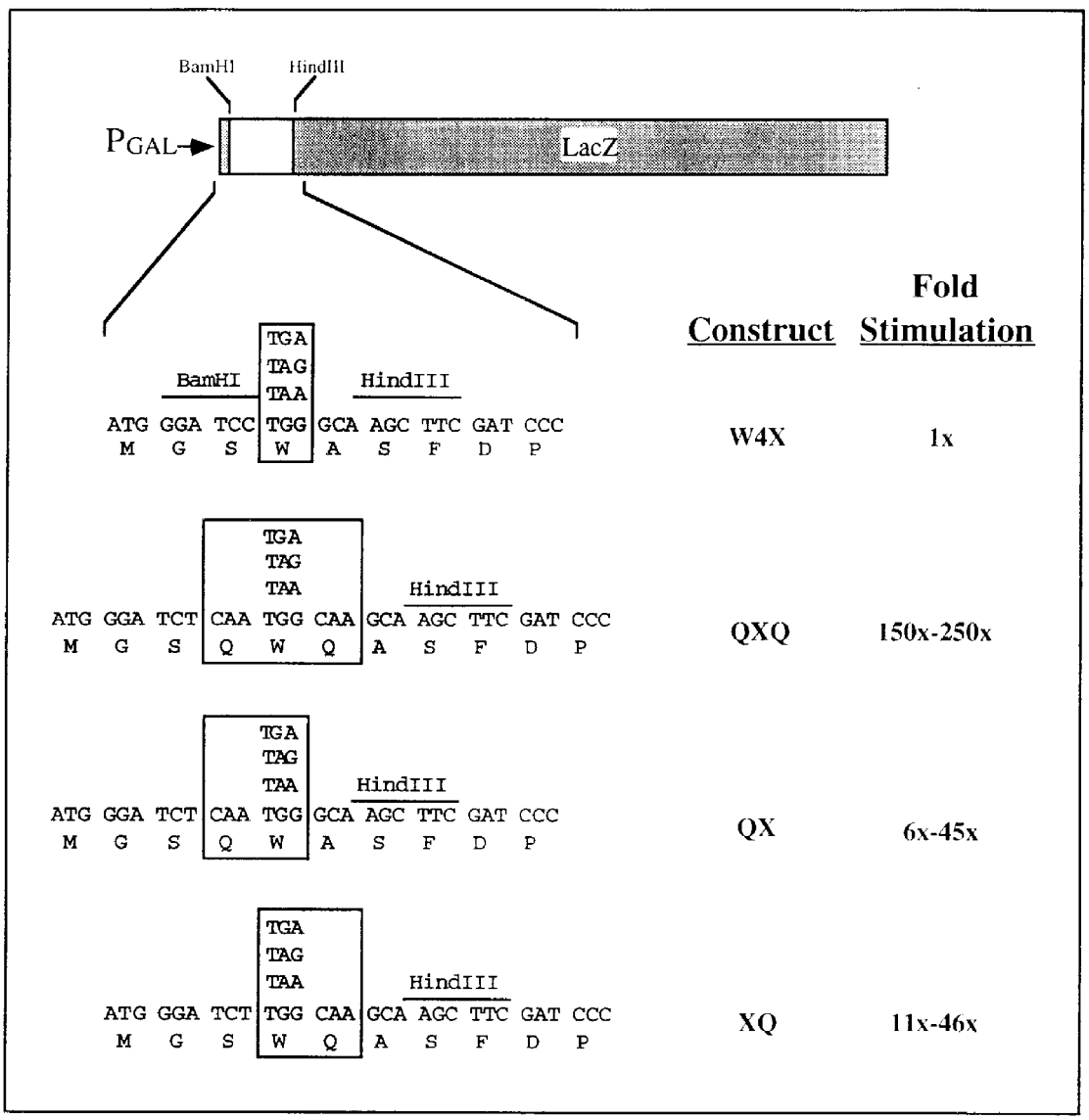
FIG. 1 shows the context-dependent suppression of premature stop mutations in yeast. "Fold stimulation" indicates the range of readthrough allowed at UAG, UGA, and UAA stop codons in each sequence context relative to the "negative control" W4X constructs. The nucleotides altered in each set of constructs are boxed.

The present invention is directed to a method of stimulating expression of a functional full-length cystic fibrosis transmembrane conductance regulator protein in an individual in need of such treatment, comprising the step of administering to said individual a pharmacologically effective dose of an aminoglycoside. Preferably, the individual has cystic fibrosis. Generally, an individual who would benefit from this specific method of the present invention has a premature stop mutation selected from the group consisting of G542X, R553X, R1162X, and W1282X. Aminoglycosides useful in stimulating the expression of a functional full-length cystic fibrosis transmembrane conductance regulator protein include gentamicin, G418, hygromycin B, paromomycin, tobramycin and lividomycin A. When administered for this method, gentamicin is administered in a dose of from about 1.0 mg/kg to about 500 mg/kg. Similarly, G418 is administered in a dose of from about 1.0 mg/kg to about 1000 mg/kg. Determination of the appropriate dosages of other useful aminoglycosides is well within the level of those having ordinary skill in this art.

The present invention is directed to a method of treating cystic fibrosis in an individual in need of such treatment, comprising the step of administering to said individual a therapeutically effective dose of an aminoglycoside. Preferably, for this method of the present invention, the aminoglycoside is selected from the group consisting of gentamicin, G418, hygromycin B, paromomycin, tobramycin and lividomycin A.

In the novel method of treating cystic fibrosis described herein, gentamicin may be administered in a dose of from about 1.0 mg/kg to about 500 mg/kg. Similarly, G418 is administered in a dose of from about 1.0 mg/kg to about 1000 mg/kg. As used herein, the term "therapeutically effective" within the context of the present method of treating cystic fibrosis shall mean a treatment capable of restoring cAMP-dependent chloride conductance and/or relieve one or more of the well known clinical manifestations of cystic fibrosis.

In the novel method of treating cystic fibrosis described herein, the aminoglycoside suppresses a premature stop mutation. Preferably, the premature stop mutation is selected from the group consisting of G542X, R553X, R1162X, and W1282X. The present invention is directed to a method of screening for a drug useful in the treatment of an individual having cystic fibrosis, comprising the step of determining said drug's ability to suppress premature stop mutations in a model of cystic fibrosis.

The present invention is directed to a method of pharmacologically suppressing premature stop mutations in an individual having such mutations, comprising the step of administering to said individual a pharmacologically effective dose of an aminoglycoside, said aminoglycoside is selected from the group consisting of gentamicin, G418, hygromycin B, paromomycin, tobramycin and lividomycin A.

The following examples are given for the purpose of illustrating various embodiments of the invention and are not meant to limit the present invention in any fashion.

EXAMPLE 1

Suppression of premature stop mutations

Several reports have suggested that the pulmonary disease associated with certain premature stop mutations in the CFTR gene is less severe than would be predicted from the complete absence of full-length CFTR (Cuppens et al., 1990; Cutting et al., 1990a; and Gasparini et al., 1992). However, these observations have been controversial since the severity of the pulmonary disease in CF is variable, even among individuals carrying the same CF alleles. Others have indicated that several premature stop mutations usually cause severe CF since they result in a greatly reduced level of CFTR mRNA (Hamosh et al., 1991; 1992). To resolve this controversy, the efficiency of premature stop mutations was investigated to determine whether they can be suppressed in a model system at significant frequencies.

During the last few years, a yeast protein called Ste6p has been used to study the basic functional characteristics of ATP binding cassette (ABC) transporters. A common feature of Ste6p, CFTR, and essentially all ABC transporters is the highly conserved leucine-serine-glycine-glycine-glutamine (LSGGQ) sequence found within their nucleotide binding domains (NBDs). Two premature stop mutations near this region occur at the glycine residue at position 542 (G542X) and the arginine residue at position 553 (R553X). Based on amino acid sequence alignments, CFTR residue R553 corresponds to the glutamine residue at position 511 (Q511) of Ste6p. Since the homology within the ABC transporters is most significant within the LSGGQ region, whether premature stop mutations at Q511 of Ste6p could be suppressed at a significant frequency was examined. Consequently, the glutamine codon at position 511 of the STE6 gene was changed to each of the stop codons (Q511UAG, Q511UAA, or Q511UGA) using site-directed mutagenesis. Low copy plasmids carrying these mutant genes were transformed into ΔSte6 yeast strains, and the ability of these mutant STE6 alleles to encode products capable of promoting yeast mating was assayed. A significant level of mating (>10% of wild type) was mediated by the Ste6p Q511X constructs, while no mating was detected in the ΔSte6 control strain. In a previous study it was shown that the first half of Ste6p (including the first six membrane-spanning domains and the first NBD of Ste6p, terminating at residue 694) is totally inactive in mating assays (Berkower and Michaelis, 1991). This suggested that the Q511X stop codons were being suppressed, resulting in the synthesis of functionally significant amounts of full-length Ste6p.

To confirm that suppression of translation termination was occurring, next examined was whether full length Ste6p could be detected immunologically in extracts prepared from ΔSte6 strains expressing each of the Ste6p Q511X constructs from plasmids. Strains were metabolically labeled with [$^{35}$S] methionine/cysteine and cell extracts were subjected to immunoprecipitation using antisera specific for Ste6p followed by SDS-PAGE. A band corresponding to full length Ste6p could be detected in strains expressing each of the Q511X constructs, although in each case the signal was weaker than the wild type Ste6p control. This band was completely absent from the same ΔSte66 strain carrying the plasmid vector alone, confirming the specificity of the antisera used. These results confirmed that translation termination was being suppressed at significant levels in each of these constructs.

Next, the frequency at which each of these premature termination codons was suppressed was quantitatively determined. However, the recovery of Ste6p in immunoprecipitation experiments (like CFTR) is somewhat variable due to its extreme hydrophobic nature, making it difficult to accurately determine the level of readthrough. To circumvent this problem, an assay system was constructed that allowed one to accurately quantitate readthrough by measuring the enzymatic activity of the reporter enzyme β-galactosidase. This system allowed restriction fragments containing stop codons to be cloned in-frame between an AUG translation initiation codon and the β-galactosidase structural gene (beginning at codon 10 of the lacZ gene), with transcription driven by the GAL 1 promoter (FIG. 1).

Negative control plasmids were initially constructed in which nine codons were fused to the coding sequence of β-galactosidase. At the fourth codon, these constructs contained either a tryptophan codon (W4UGG) or the amber (W4UAG), ochre (W4UAA), or opal (W4UGA) termination codons. These constructs are collectively called the W4X constructs (see FIG. 1). When β-galactosidase activity was examined in strains expressing these constructs, it was found that the W4UGG construct had high β-galactosidase activity, while each of the three constructs with in-frame stop codons exhibited β-galactosidase activity that was 6,000–10,000 fold lower. This extremely low level of readthrough (0.01–0.02% of a sense codon) indicated that this assay system could accurately reflect the efficient translation termination found at naturally occurring stop codons.

Next, a 141 base pair XbaI fragment (containing residues 1935–2081 of the STE6 structural gene) was inserted that encoded either the wild type glutamine codon (XbaI-Q511CAA) or one of the three stop codons at the same position (XbaI-Q511UAG, XbaIQ-511UAA, or XbaI-Q511UGA, collectively called XbaI-Q511X constructs) into the readthrough assay system. The four plasmids were transformed into yeast and β-galactosidase activities were again assayed. High β-galactosidase activity was again obtained for the sense (XbaI-Q511CAA) construct. However, in contrast to the control W4X constructs, each of the XbaI-Q511X constructs also showed significant β-galactosidase activity, indicating that suppression of each of the termination codons occurred in the context of the 141 base pair XbaI fragment from the STE6 gene. These values ranged from 9.8% of wild type expression for the XbaIQ-511UAG construct to 2.7% of wild type expression for the Xba-Q511UAA construct, indicating that some feature of the 141 base pair XbaI fragment was capable of mediating efficient suppression of each termination codon.

The termination codons in both the intact STE6 gene and the XbaI-Q511X fusion constructs were flanked by tandem glutamine (CAA) codons. To determine whether these adjacent glutamine codons alone contained the information required to promote readthrough, a third set of β-galactosidase fusion constructs was prepared in which glutamine (CAA) codons were inserted on either side of the termination codons in the W4X plasmids described above. These QXQ constructs (see FIG. 1) encoding glutamine codons flanking either a tryptophan codon (QXQ-UGG) or one of the three stop codons (QXQ-UAG, QXQ-UAA, or QXQ-UGA) at position 5 were then transformed into yeast, and β-galactosidase activity was again assayed. As expected, high level β-galactosidase activity was obtained for the QXQ-UGG construct. When the QXQ plasmids containing in-frame stop codons were assayed, significant levels of termination suppression were again observed. The introduction of three flanking nucleotides (CAA) on both sides of the termination codon was sufficient to cause a several hundred fold decrease in the efficiency of translation termination, resulting in a level of readthrough as high as 16% of a sense construct (FIG. 1). This indicated that in this context, readthrough could occur as frequently as once every 6 times a ribosome encountered the premature stop codon. In addition, it was found that this phenomenon was not codon specific, since this context significantly decreased the efficiency of translation termination at each of the three termination codons. Additional experiments indicated that the presence of either the upstream context (OX constructs) or downstream context (QX constructs) was each sufficient to provide intermediate levels of readthrough (FIG. 1). These results indicate that the upstream and downstream determinants act synergistically to influence the overall efficiency of translation termination.

It was then determined how suppression of these premature stop mutations occurred. Since readthrough of the stop codon in the QXQ constructs occurred near the amino terminus of the protein, the fusion proteins encoded by these constructs represented good candidates for protein sequence analysis. Approximately two hundred pmoles of the β-galactosidase fusion protein produced by readthrough of the QXQ-UAG construct were purified by immunoaffinity chromatography and subjected to automated Edman degradation. Primary sequence data indicated that tyrosine, lysine, and tryptophan were inserted in significant amounts above background at position 4, indicating that misincorporation of these amino acids resulted in the translational suppression of the amber termination signal. The incorporation of these amino acids indicated that readthrough was mediated by near-cognate tRNA mispairing, in which an aminoacyl tRNA bases pairs at only two of the three positions of the termination codon.

EXAMPLE 2
Aminoglycoside-induced suppression of stop mutations

Studies in the mid-1960s demonstrated that low concentrations of aminoglycoside antibiotics such as streptomycin, neomycin, and gentamicin can induce ribosomal misreading in E. coli (Davies et al., 1965). Aminoglycoside-mediated misreading was shown to cause both an increased rate of misincorporation at sense codons and an increased level of readthrough of stop codons. In addition, mutants studied by Gorini have shown that translational accuracy can be altered in either direction, indicating that protein synthesis in E. coli is not optimized for accuracy (Gorini, 1974). These studies also demonstrated that bacterial cells could tolerate a certain level of general misreading in order to achieve the synthesis of physiologically significant levels of a readthrough product required for growth, indicating that a moderate reduction in the fidelity of translation did not have a significant effect on cell viability.

TABLE 1

Context dependence of aminoglycoside-mediated suppression of premature stop mutations

|  | W4X Context | | | OXO Context | | |
| --- | --- | --- | --- | --- | --- | --- |
| Aminoglycoside | UAG | UGA | UAA | UAG | UGA | UAA |
| Control | 1.0 | 1.0 | 1.0 | 1.0 | 1.0 | 1.0 |
| Hygromycin B | 16.5 | 18.3 | 16.7 | 1.3 | 2.2 | 2.1 |
| Paromomycin | 8.1 | 10.0 | 5.9 | 3.7 | 3.7 | 6.8 |
| G-418 | 4.7 | 9.6 | 4.3 | 0.8 | 1.1 | 1.3 |
| Gentamicin | 1.9 | 3.0 | 2.2 | 1.7 | 2.9 | 2.0 |
| Tobramycin | 1.4 | 3.4 | 1.6 | 0.9 | 0.9 | 0.9 |
| Lividomycin A | 2.1 | 2.8 | 1.3 | 1.4 | 1.2 | 1.5 |
| Neomycin B | 1.4 | 1.4 | 1.2 | 1.1 | 2.8 | 1.3 |
| Amikasin | 1.3 | 1.0 | 1.7 | 1.2 | 1.2 | 0.8 |
| Kanamycin A | 1.0 | 1.0 | 0.7 | 1.1 | 1.1 | 1.1 |
| Sisomycin | 1.4 | 1.0 | 3.5 | 1.0 | 1.2 | 1.5 |

Values represent the fold stimulation of readthrough mediated by the indicated aminoglycoside relative to the untreated control.

Aminoglycoside-induced misreading has also been shown to occur in yeast. For example, aminoglycoside antibiotics such as paromomycin and hygromycin B were found to induce the suppression of premature stop mutations (Singh et al., 1979; Palmer et al., 1979). The readthrough assay constructs were used to examine the context dependence of aminoglycoside-mediated suppression of stop mutations (TABLE 1). Some aminoglycosides, such as hygromycin B, show a relatively strong context dependence. Hygromycin B can stimulate readthrough of a stop codon in the W4X context to a much greater extent than a stop codon in the QXQ context. This compound may act to reduce the recognition of the extended termination sequence by the polypeptide chain release factor. However, other compounds, such as paromomycin, G-418, and gentamicin mediated a more moderate and uniform level of suppression in both sequence contexts. Other aminoglycosides had less significant effects on the level of readthrough in either context. The relative inability of these compounds to promote readthrough could be due to permeability problems, resulting in an inability to efficiently enter the cell. Alternatively, these compounds may be less efficient at interacting with the translational apparatus in a manner that leads to suppression.

EXAMPLE 3
Premature stop mutations in CFTR

As discussed above, several reports have suggested that the pulmonary disease associated with certain premature stop mutations in the CFTR gene may be less severe than would be predicted from the complete absence of full-length CFTR (Cuppens et al., 1990; Cutting et al., 1990; and Gasparini et al., 1992). However, these observations have been controversial since the severity of the pulmonary disease in CF can be quite variable, even among individuals carrying the same CF alleles. While this variability may be attributable to unlinked genetic determinants, environmental factors may also play a role. Based upon the results presented above, one possible environmental factor affecting the severity of CF in patients with premature stop mutations may be the use of aerosolized aminoglycoside antibiotics during regularly scheduled treatments (termed "cleanouts") to combat recurring bacterial lung infections. The present invention demonstrates that aminoglycosides can induce the synthesis of full-length, functional CFTR in human cells.

Whether the sequence context surrounding disease-causing premature stop mutations in CFTR can result in a significant level of readthrough was examined. To do this, the production of full-length CFTR from cDNAs introduced into HeLa cells was initially assayed. The mutations examined, G542X and R553X, each introduce an in-frame ochre (UGA) stop codon near the end of the first nucleotide binding domain of CFTR (Cutting et al., 1990; Kerem et al., 1990). HeLa cells infected with Vaccinia-T7 were co-transfected with the plasmid vector pTM1 carrying the indicated CFTR allele under T7 promoter control (Fuerst et al., 1986; Howard et al., 1995). Following transfection of a wild type CFTR cDNA into Vaccinia-T7 infected HeLa cells, wild type CFTR expression was readily detected both by immunoprecipitation and with a halide permeability assay using the fluorescent dye, SPQ (Yang et al., 1993). However, neither full-length CFTR nor an increase in halide efflux from cells transfected with cDNAs containing either the G542X or the R553X mutations were detected. This indicated that readthrough of these premature stop mutations (to the extent detectable by these assays) does not occur under normal conditions.

Figure 2A:
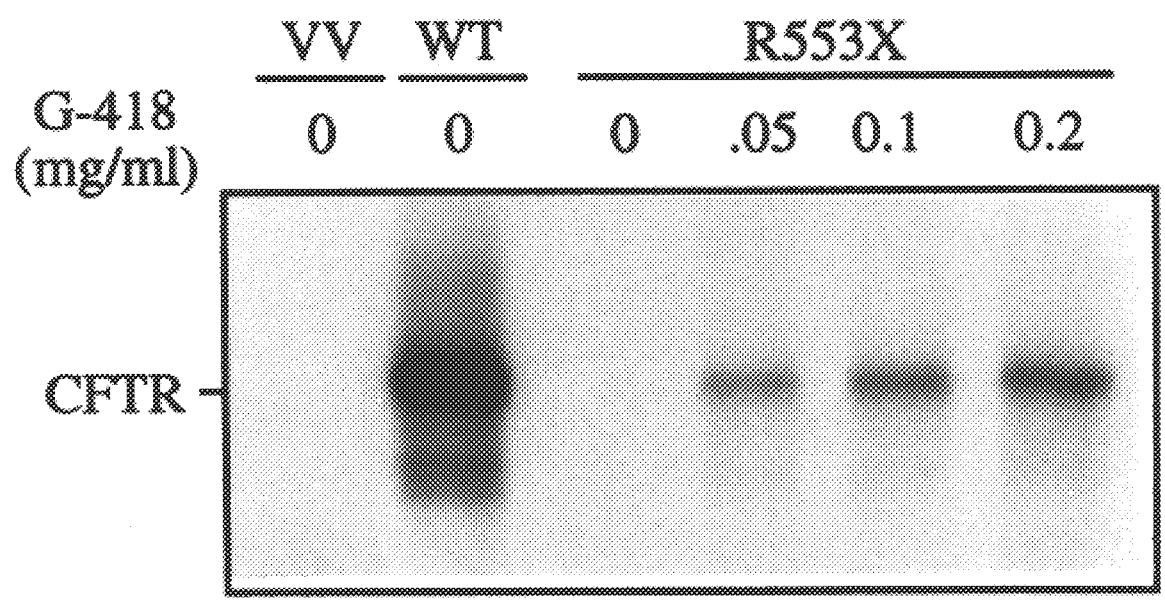
FIG. 2A shows the dose-dependent translational readthrough of the R553X mutation with increasing G-418 concentration.
Figure 2B:
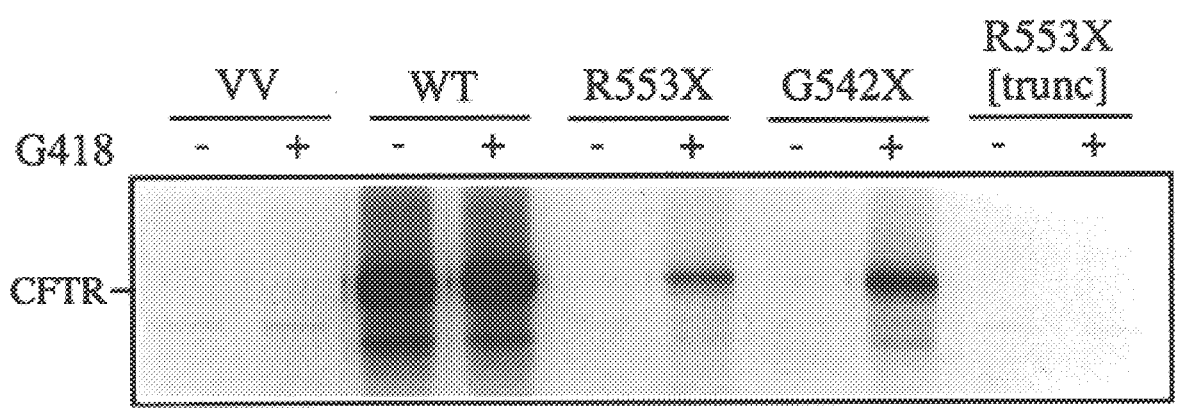
FIG. 2B shows the suppression of the G542X and R553X mutations by 0.1 mg/ml G-418.

Whether the suppression of premature stop mutations could be induced by aminoglycoside treatment was examined. Cells transfected with the CFTR R553X construct were incubated with different concentrations of the aminoglycoside G-418 for 8–12 hours. A dose-dependent increase was observed in the expression of full-length CFTR from the R553X mRNA as a function of G-418 concentration, indicating that G-418 stimulates readthrough of the R553X mutation (FIG. 2A). Quantitation of different experiments indicated that the amount of full-length CFTR produced was as much as 25% of the level of protein expression obtained from the wild type CFTR cDNA. Even more full-length CFTR (as much as 35% of wild type) was observed in cells transfected with the CFTR G542X cDNA (FIG. 2B), indicating that G-418 also promotes readthrough of this second CFTR mutation. G542X is the most common premature stop mutation found in CF patients (Cutting, 1993; CF Genetic Analysis Consortium, 1994). In contrast, full-length CFTR was not detected in cells expressing a 5' portion of the CFTR R553X cDNA truncated after the codon for amino acid 699 of CFTR. This confirmed that the intact CFTR cDNA was required for expression of the translation product observed upon G-418 treatment.

Figure 3A:
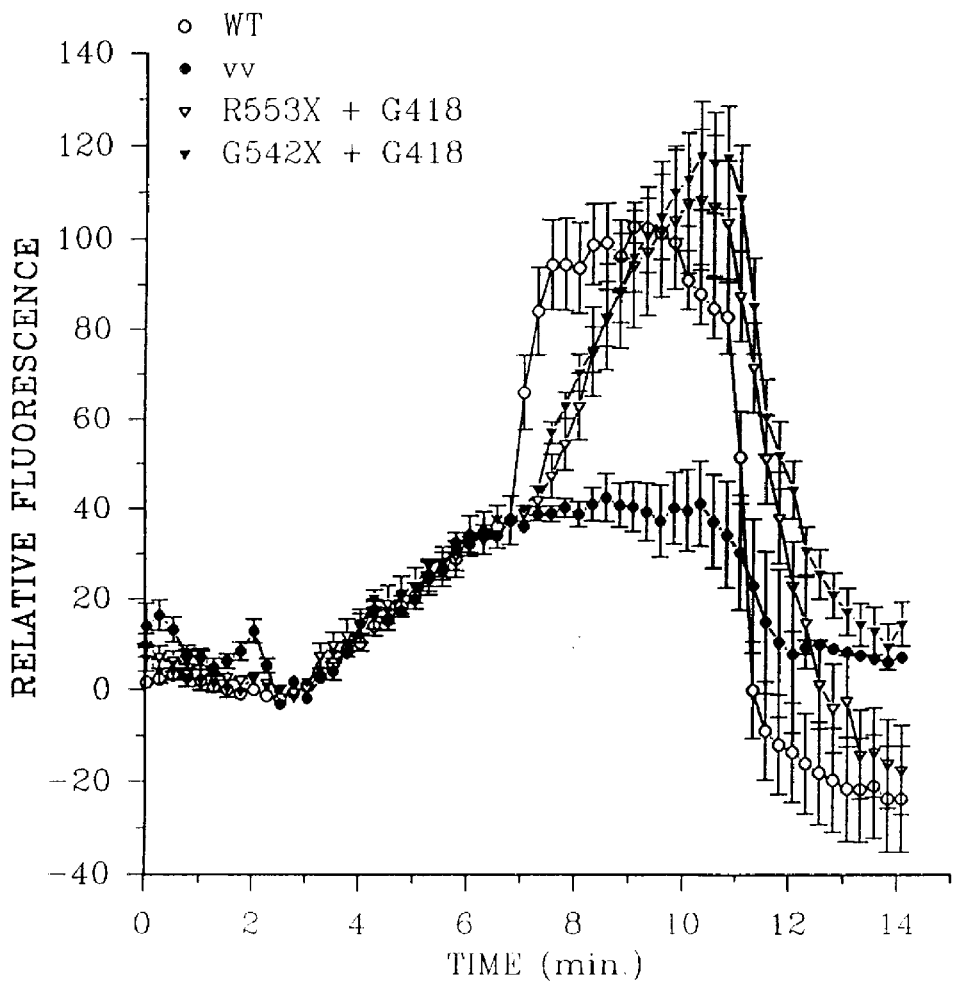
FIG. 3A shows that G-418 increases cAMP-stimulated chloride channel activity in cells expressing the G542X or R553X cDNAs.

As discussed above, it was shown that the suppression of premature stop mutations occurs through a mechanism of near cognate mispairing of an aminoacyl-tRNA with the premature stop codon (Fearon et al., 1994). Since the amino acid inserted by this mechanism may differ from the amino acid encoded in the wild type protein, whether CFTR's function as a cAMP-activated chloride channel was also recovered upon G-418 treatment using the SPQ assay was examined (FIG. 3A). cAMP treatment of cells transfected with the wild type CFTR cDNA caused a rapid increase in SPQ fluorescence, consistent with stimulation of CFTR-mediated halide efflux. This response required CFTR expression, since no increase in fluorescence was observed when cells infected with vaccinia-T7 alone were treated with cAMP. As discussed above, cells expressing either the G542X or R553X cDNAs in the absence of aminoglycosides showed no cAMP-dependent increase in anion permeability. However, following incubation with G-418, cAMP induced a significant anion efflux in cells transfected with either the G542X or R553X cDNA. This indicates that the full-length CFTR expressed from these mutant constructs following aminoglycoside treatment also functions as a cAMP-stimulated anion channel.

Figure 3B:
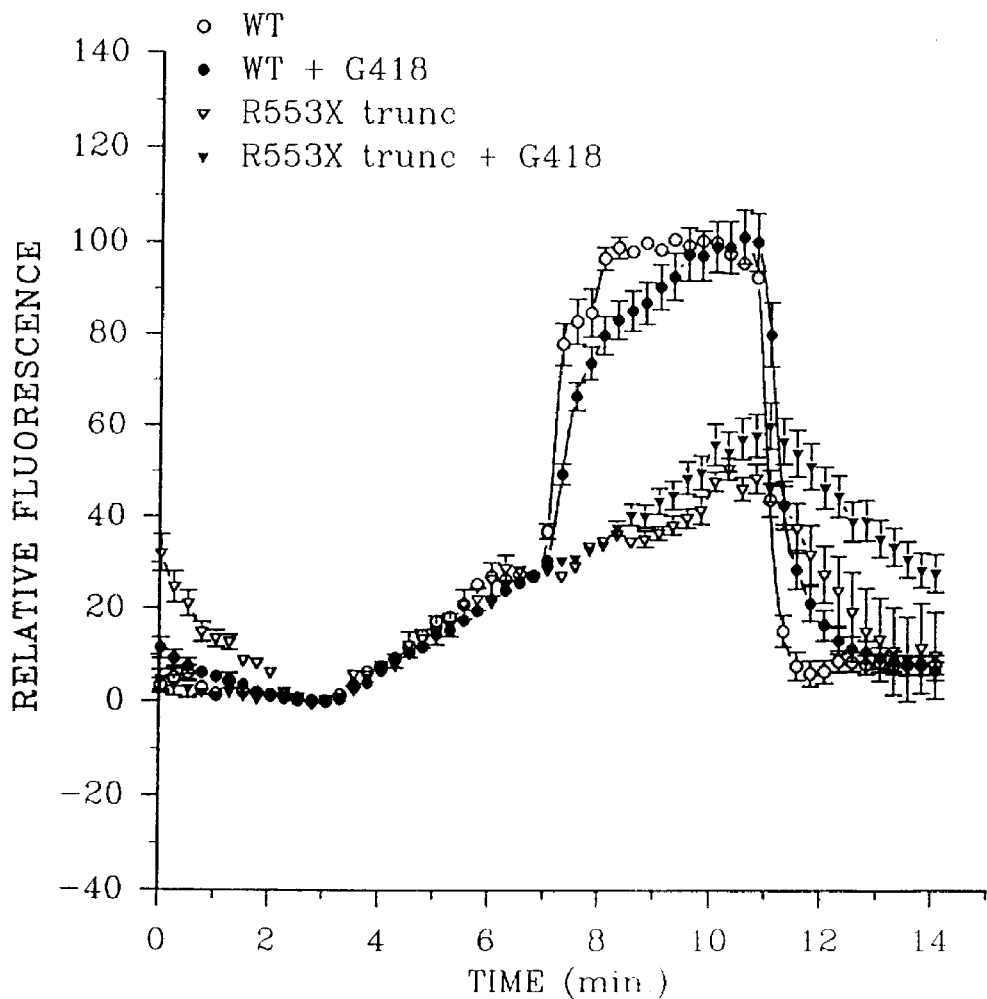
FIG. 3B shows that G-418 stimulation of chloride channel activity requires an intact CFTR cDNA. Cells were initially loaded in a hypotonic buffer containing SPQ and sodium iodide; iodide quenches SPQ fluorescence (Yang et al., 1993). Sodium iodide in the bath was replaced by sodium nitrate at 2 min; since nitrate does not interact with SPQ, fluorescence increases as cell iodide is lost to the bath. A cAMP stimulation cocktail (10 mM forskolin, 100 mM cpt-cAMP and 100 mM IBMX) was added at 6 min. Fluorescence was then quenched again by returning sodium iodide to the bath at 10 minutes. Functional CFTR expression was monitored as the dequenching of SPQ fluorescence caused by cAMP-induced iodide efflux. To truncate the CFTR R553X cDNA distal to the premature stop mutation, the plasmid was digested with EcoRI and SacI. The cohesive ends were removed by treatment with the Klenow fragment of DNA polymerase I and the plasmid was then religated. This treatment removed the CFTR structural gene from the EcoRI site at position 2230 through the SacI site at position 4651 (76 nucleotides beyond the natural termination codon). This resulted in the removal of the distal 2346 nucleotides of the coding sequence in the CFTR cDNA.

It was previously shown that following the overproduction of an amino terminal portion of CFTR containing the first membrane domain, the first nucleotide binding domain, and the R domain (terminating at amino acid 836) a partially regulated chloride channel could be detected (Sheppard et al., 1994). This raised the possibility that the truncated forms of CFTR produced by translation termination at either residue 542 or 553 might be activated to a functional state by aminoglycoside treatment. Whether cAMP-activated anion efflux could be induced in cells transfected with the truncated CFTR R553X cDNA (FIG. 3B) was determined. However, no cAMP-dependent anion permeability was detected in cells expressing this truncated cDNA in the presence of G418. Thus, the portion of the CFTR cDNA distal to the stop mutation is required for restoration of cAMP-activated chloride channel activity, indicating that this activity is attributable to the expression of full-length CFTR.

Figure 4:
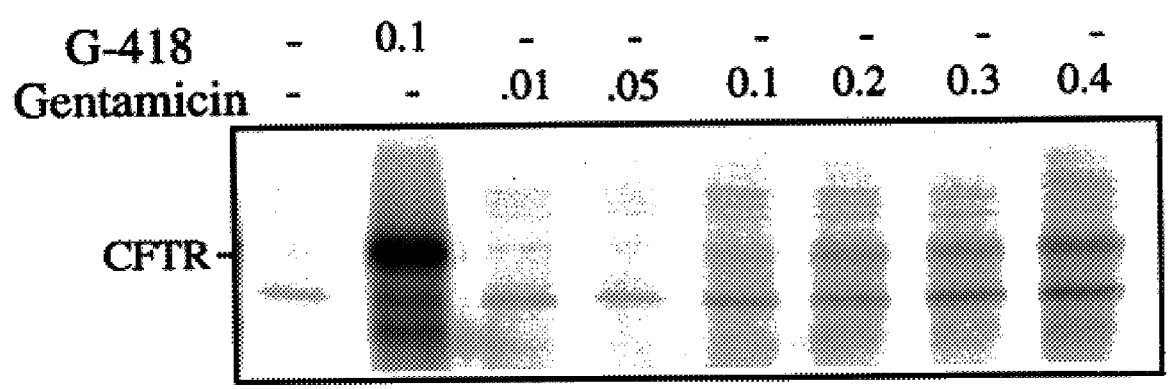
FIG. 4 shows the dose-dependent stimulation of fulllength CFTR synthesis from the CFTR R553X cDNA with gentamicin. Infections and transfections were performed as described above, except gentamicin was substituted for G-418. Gentamicin concentrations used are indicated in mg/ml.

Currently, some aminoglycosides are aerosolized into the lungs of CF patients to treat bacterial infections. To determine whether these clinical aminoglycosides are also capable of inducing readthrough in human cells, whether two commonly used compounds, tobramicin and gentamicin, could stimulate readthrough of the G542X or R553X mutations was examined. Full-length CFTR could not be detected following treatment with tobramicin, but a small amount of full-length CFTR was observed by immunoprecipitation following treatment with gentamicin (FIG. 4). However, it was not determined whether a cAMP-stimulated anion permeability accompanies the expression of this full-length product. Since the clinically relevant aminoglycosides were developed for maximal bactericidal activity, evaluation of the utility of aminoglycosides to suppress premature stop mutations necessitates a systematic re-evaluation of these compounds to identify those that can optimally stimulate readthrough with minimal toxicity. It is possible that a general increase in the suppression of stop codons might lead to the accumulation of toxic, non-functional readthrough products. However, no evidence was found that low level G-418 treatment significantly impaired any normal cellular functions. Exposure of HeLa cells expressing wild type CFTR to G-418 did not affect: 1) their functional response to cAMP stimulation; 2) the total amount of CFTR synthesized; or 3) total protein synthesis rates. Animal studies also indicate that G-418 is 2–3 fold less toxic than gentamicin when administered by either intravenous or subcutaneous routes (Waity et al., 1974). Furthermore, it is well documented that relatively efficient suppresser tRNAs that promote readthrough of stop mutations can be maintained in several organisms (including human cell lines) without adverse effects (Eggertsson and Soll, 1988; Sherman, 1982; Hatfield et al., 1990).

Premature stop mutations account for approximately 5% of the total mutant alleles in CF patients (Cutting, 1993; CF Genetic Analysis Consortium, 1994). However, in certain subpopulations the incidence of this class of mutation is much higher. For example, the W1282X premature stop mutation is the most common CF-causing mutation in the Ashkenazi Jewish population, where it is present on 60% of all CF chromosomes (Shoshani et al., 1992). Several reports have suggested that the pulmonary disease associated with several premature translation termination mutations is less severe than would be predicted from the complete absence of full-length CFTR (Cuppens et al., 1990; Cutting et al., 1990; and Gasparini et al., 1992). However, these observations have been controversial since the severity of the pulmonary disease in CF can be quite variable. It is possible that this variability is attributable to other genetic determinants unlinked to the CFTR locus. However, environmental factors could also play a role, including possible differences in the use of aminoglycoside antibiotics during routine clinical treatments.

One of the major limitations to the clinical use of aminoglycoside antibiotics is the relatively high level of systemic toxicity of these compounds. However, a recent study found that regular aerosolized delivery of tobramycin to the lower airways of CF patients is not toxic (Ramsey et al., 1993). This may be attributable to the low permeability of the drug across the airway epithelium that results in very low drug concentrations in the circulation. Thus, aerosolized delivery of aminoglycosides to the airway may also be used to promote the production of full-length CFTR through the suppression of premature stop mutations in lung epithelia. This approach would represent the first clinical treatment capable of correcting CF by restoring the expression of functional, endogenous CFTR in a specific genotypic subgroup of CF patients.

Figure 5:
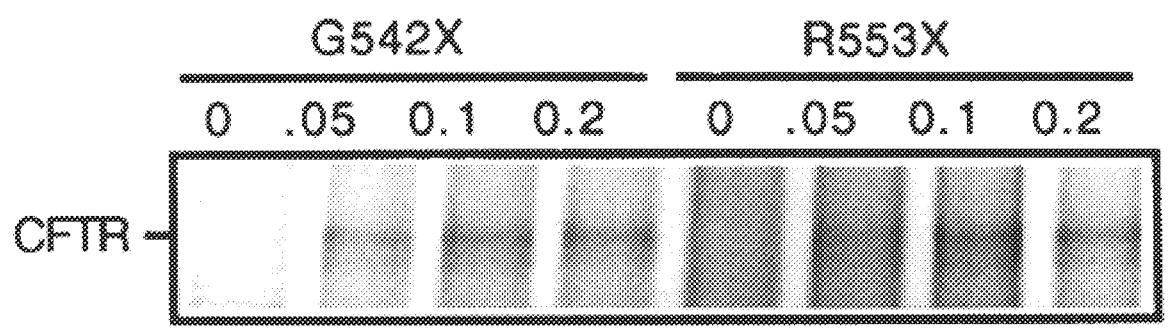
FIG. 5 shows that G-418 induces the expression of full-length CFTR from recombinant vaccinia-CFTR constructs in HeLa cells. Concentrations of G-418 used are indicated in mg/ml.

EXAMPLE 4
Use Of Aminoglycoside Antibiotics To Suppress Naturally-Occurring Premature Stop Mutations In Model CFTR Expression Systems A modified vaccinia-T7 system is used to further characterize the suppression of stop mutations that restore CFTR function. As described above, the present invention demonstrated the suppression of premature CFTR stop mutations in human cells using a vaccinia-T7 expression system. In this system, cells are first infected with the vaccinia-T7 virus. These vaccinia infections are quite efficient and almost all cells routinely take up the virus. The infected cells are subsequently transfected with the plasmid vector pTM1 containing the various CFTR cDNAs, a procedure that is much less efficient and somewhat variable. The vaccinia system was chosen primarily because of the high level of expression possible, which made it more likely that low level readthrough products could be detected. However, one disadvantage of the version of the system used is the variability in transfection efficiencies obtained from different CFTR cDNAs within the same experiment, which made a quantitative analysis of the resulting data difficult. To circumvent this problem, a modified expression system was constructed in which the various CFTR cDNA constructs have been recombined directly into the vaccinia-T7 viral genome. The suppression of the G542X and R553X stop mutations by aminoglycoside treatment can still be observed using this modified vaccinia-CFTR system (FIG. 5). Consequently, all subsequent vaccinia-based studies of the suppression of premature stop mutations in CFTR will use this more efficient (and quantitative) system.

It has been shown that four premature stop mutations (G542X, R553X, R1162X and W1282X) are among the most common CF-causing mutations (after ΔF508). The two mutations located in the first NBD, G542X and R553X, can be suppressed. Two distal mutations (R1162X and W1282X) generated using a PCR mutagenesis assay are created and treated with aminoglycoside to suppress these mutations. As before, assays used to monitor readthrough will include both immunoprecipitation to detect full-length CFTR and SPQ assays to monitor CFTR function. Overproduction of an amino terminal portion of CFTR containing only the first membrane domain, the first nucleotide binding domain, and the R domain (terminating at amino acid 836) results in a partially regulated chloride channel (Sheppard et al., 1994). Thus, it is possible that some cAMP-activated halide efflux may be detected before aminoglycoside treatment from constructs expressing a CFTR cDNA containing these late stop mutations. However, distal premature stop mutations are associated with a severe reduction in CFTR mRNA (Hamosh et al., 1991; 1992). Furthermore, studies of the immortalized cell line IB3-1 derived from a compound heterozygote (DF508/W1282X) indicated that no cAMP-stimulated channel activity could be detected (Zeitlin et al., 1991). These results suggest that little or no cAMP-stimulated halide efflux will be seen prior to aminoglycoside treatment.

One potential criticism of the vaccinia-CFTR assay system is related to the observation that the integrity of vaccinia-infected cells becomes compromised as the viral infection progresses. This raises the possibility that the entry of aminoglycosides to the levels required to induce readthrough may not occur in uninfected cells. Readthrough and CFTR function were determined at an early stage of infection before significant morphological changes occurred. The integrity of the plasma membrane under these conditions is indicated by the sharp increase in fluorescence upon cAMP activation in the SPQ assays (see FIG. 3), demonstrating that the plasma membrane remains relatively impermeable to iodide until CFTR is activated.

The modified vaccinia-CFTR assay system is used to examine the efficacy of aminoglycosides other than G-418 and gentamicin. As demonstrated above, different aminoglycosides have widely differing abilities to suppress stop mutations in a yeast readthrough assay system. The vaccinia-CFTR system is used to examine a collection of aminoglycosides previously analyzed in the yeast system. As before, the lowest concentration of each drug that inhibits cell growth is determined, and then assayed for the ability to induce readthrough at levels below that inhibitory concentration. Immunoprecipitations and SPQ assays is used to detect readthrough of the stop mutations.

EXAMPLE 5
Suppression of premature stop mutations in Xenonus oocytes

The vaccinia-CFTR system described above has already proven useful in testing the feasibility of the pharmacological suppression of premature stop mutations. However, other CFTR expression systems are also used. Since the expression of CFTR in Xenopus oocytes provides a simple assay system to initially examine the electrophysiological characteristics of CFTR expressed following aminoglycoside treatment, the oocyte system is used to examine the level of channel activity (relative to the wild type control) that can be induced by aminoglycoside treatment.

Figure 6:
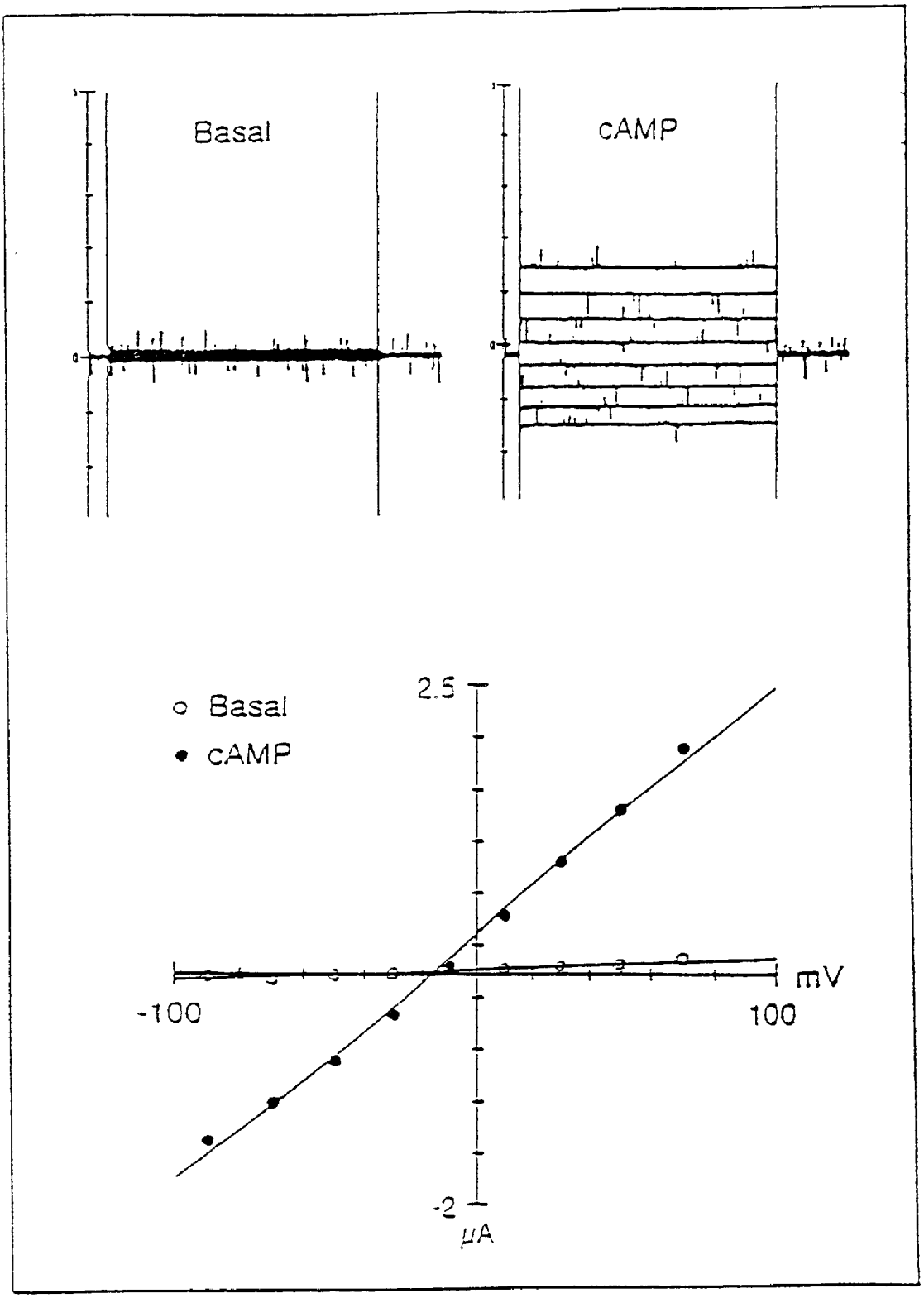
FIG. 6 shows the expression of wild type CFTR in $Xenopus\ laevis$ oocytes. Current-voltage (I–V) relationships were evaluated by two-electrode voltage-clamp two days after oocytes were injected with wild type CFTR mRNA (5 ng in a 5 nl volume). Oocytes were bathed in ND96 solution at 20° C. This solution contained (in mM): 96 NaCl, 1 KCl, 1.2 $CaCl_2$, 5.8 $MgCl_2$, and 10 HEPES; pH 7.4. Membrane potentials were allowed to stabilize following impalement (~10 min) after which the membrane potential was clamped and held at −20 mV. The I–V relationships were generated by clamping from the holding voltage (−20 mV) to −90 through +70 mV in 20 mV increments under basal conditions (top left) and after 15 min perfusion with a cAMP cocktail (10 $\mu$M forskolin and 1 mM 3-isobutyl-1-methylxanthine; top right). The slope of the I–V relationship represents the whole-cell conductance. As indicated by the bottom figure, the conductance under basal conditions was 0.9 $\mu$S and increased to 21 $\mu$S following perfusion with the cAMP cocktail.

Restriction fragments carrying the CFTR-G542X and CFTR-R553X constructs were already transferred into the CFTR expression plasmid pBQ4.7, which allows the synthesis of CFTR mRNA from the bacteriophage T7 promoter. These constructs (or constructs containing the R1162X or W1282X mutations) are used to generate CFTR mRNA suitable for microinjection into Xenopus oocytes using a commercially available in vitro transcription kit (Ambion). To assay for the expression of functional CFTR, oocytes are injected with either wild type or mutant CFTR mRNAs. The injected oocytes are allowed to express the encoded protein for two days, and are then treated with aminoglycosides and assayed for the appearance of a cAMP-activated chloride channel activity. Wild type CFTR mRNA was synthesized and this mRNA can produce significant cAMP-stimulated chloride currents characteristic of CFTR (FIG. 6).

Initially, the appearance of cAMP-activated chloride currents is determined in oocytes injected with the mutant mRNAs following the addition of aminoglycosides to the incubation bath. A time course experiment determines the incubation period with the drug that provides the maximal level of CFTR expression. The ion selectivity and the rectification of the channel are measured to determine whether the induced channels exhibit the basic electrical properties of wild type CFTR. Following these experiments, the magnitude of the cAMP-activated currents following aminoglycoside treatment is quantitated and these values are normalized to oocytes injected with wild type CFTR mRNA to determine the relative level of CFTR activity obtained. In these experiments, it is possible that the truncated protein product (which is truncated well before the R domain in the G542X and R553X constructs) will result in a basal, constitutively activated ion conductance.

EXAMPLE 6
Analysis of CFTR activity resulting from aminoglycoside-mediated suppression in transfected cell lines Having established the basic requirements for suppression of stop mutations within the CFTR cDNAs and the functional characteristics of the readthrough products obtained using the systems described above, the electrophysiological properties of the channels induced by aminoglycoside treatment in transfected mammalian cells are analyzed. First, the CFTR wild type, CFTR-G542X, or CFTR-R553X cDNAs are cloned into the expression vector pGT-1. This vector drives transcription from the SV40 early promoter. The CFTR wild type, CFTR-G542X, or CFTR-R553X constructs are transfected into Cos-7 cells. The transfected cells are allowed to grow for a day, and are incubated in the presence or absence of various aminoglycosides for 1–2 days. The cells are examined for both total chloride currents and the appearance of cAMP-inducible chloride currents by cell attached recording. First, the total and DIDS-sensitive chloride currents are determined. DIDS effectively blocks most chloride channels (including the ORCC) at concentrations that do not significantly inhibit CFTR (Schwiebert et al., 1994). Under conditions that inhibit the DIDS-sensitive current, whether a cAMP-stimulated chloride current (indicative of CFTR) can be detected in cells incubated in the presence of aminoglycosides is determined. This induced current should be inhibited by 100–300 mM DPC if it corresponds to CFTR. If the appearance of such a cAMP-stimulated current with the general characteristics of CFTR can be detected in cells transfected with the stop mutant constructs following aminoglycoside treatment, it would indicate that the expression of full-length CFTR had been induced by suppression of the premature stop mutation.

EXAMPLE 7
Aminoglycoside-Based Suppression Of Premature Stop Mutations In Cells Expressing CFTR From The Nuclear Genome The in vivo situation leading to the synthesis of CFTR is complex. First, the expression of CFTR in lung epithelial cells requires the transcription of a nuclear gene that extends roughly 250 kilobases. Next, the primary CFTR transcript must be processed to the mature transcript by the excision of 26 introns, reducing the size of the mRNA to roughly 6.5 kilobases. Finally, export of the matured mRNA from the nucleus must occur before cytoplasmic ribosomes can initiate the synthesis of CFTR.

The steady-state level of mRNAs containing a premature stop mutation are often reduced when compared to the corresponding wild type mRNA (Maquat, 1995). Interestingly, this instability is often manifested as a decrease in the stability of the immature, nuclear form of the mRNA as well as a decrease in the stability of the mature mRNA in the cytoplasm. This suggests that some mechanism scans the proper reading frame of the mRNA for stop mutations before splicing and nuclear export are completed. Two models have been brought forward to explain this observation (Urlaub et al., 1989). In the first model, a machinery exists in the nucleus that can scan the proper reading frame of the mRNA prior to the completion of splicing and export. If an in-frame premature stop codon is detected by this mechanism, the splicing process is interrupted and the nascent mRNA molecule is rapidly degraded. However, it is conceptually difficult to justify the existence of such a complicated apparatus within the nucleus to ensure that premature stop mutations are not present. In the second model, the processes of mRNA splicing, export, and translation are temporally coupled. Because of this coupling, translation at the 5' of the mRNA can begin in the cytoplasm before the processing and export of the mRNA within the nucleus is completed. The normal translational activity of the ribosome can then survey the proper reading frame of the encoded polypeptide chain during the process of protein synthesis. If the ribosome encounters an in-frame premature stop codon, translation is terminated, the nascent chain is released by polypeptide chain release factor, and the ribosome dissociates from mRNA. In this model, premature translation termination also causes a signal to be transmitted to the nucleus to abort the splicing and export processes and to degrade the immature, defective mRNA. Consistent with this model, the stability of mammalian mRNAs that contain a premature stop mutation can be increased by various manipulations that prevent translation termination (Beigrader et al., 1993). For example, suppression of the premature stop mutation by a suppresser tRNA has been shown to stabilize the mRNA and allow the completion of mRNA maturation. In addition, a general decrease in the level of translation caused by the introduction of a 5' hairpin structure also stabilizes the production of the mature mRNA, suggesting that the frequency of premature translation termination plays a key role in influencing mRNA stability.

These observations have important implications for the suppression of premature stop mutations in the CFTR gene. Several premature stop mutations in CFTR result in a reduced steady-state level of CFTR mRNA (Hamosh et al., 1991; 1992). However, since approaches that reduce the frequency of translation termination have the capacity to restore mRNA stability, it is quite possible that the process of suppressing premature stop mutations with aminoglycosides will partially (or completely) restore the steady-state level of CFTR mRNA. Furthermore, several studies have shown that stop mutations near the 5' end of a gene destabilize various mRNAs to a much greater extent than stop mutations near the 3' end of the gene (Brown, 1993). This suggests that premature stop mutations near the 3' end of the CFTR gene (such as the R1162X and W1282X mutations) may be less susceptible to mRNA destabilization than mutations that occur closer to the 5' end of the transcript.

EXAMPLE 8
Aminoglycoside-based suppression of premature stop mutations in an immortalized cell line derived from a patient carrying the W1282X mutation To demonstrate that one can restore CFTR expression in cells containing premature CFTR stop mutations in the genome, a premature stop mutation is suppressed in the immortalized bronchial epithelial cell line, IB3-1. This cell line was derived from a CF patient carrying the ΔF508 mutation on one chromosome and the late premature stop mutation W1282X on the other (Zeitlin et al., 1991). This cell line was shown to retain the ability to produce cAMP. In addition, chloride conductance could not be activated by either PKA or PKC, but could be activated by the application of a depolarizing voltage of 50 mV or greater across the patch. This is consistent with the absence of CFTR in these cells, but the continued presence of the outwardly rectified chloride channel (ORCC). Furthermore, CFTR mRNA can be detected by RT-PCR, and endogenously expressed CFTR can be detected by immunocytochemistry in a perinuclear region with the anti-R domain antibody. This protein probably represents the ΔF508 protein in the ER, although it could also include some truncated protein expressed from the W1282X allele. Thus, these cells are still capable of expressing CFTR and provide an ideal system to show suppression of a premature stop mutation in CFTR.

Figure 7A:
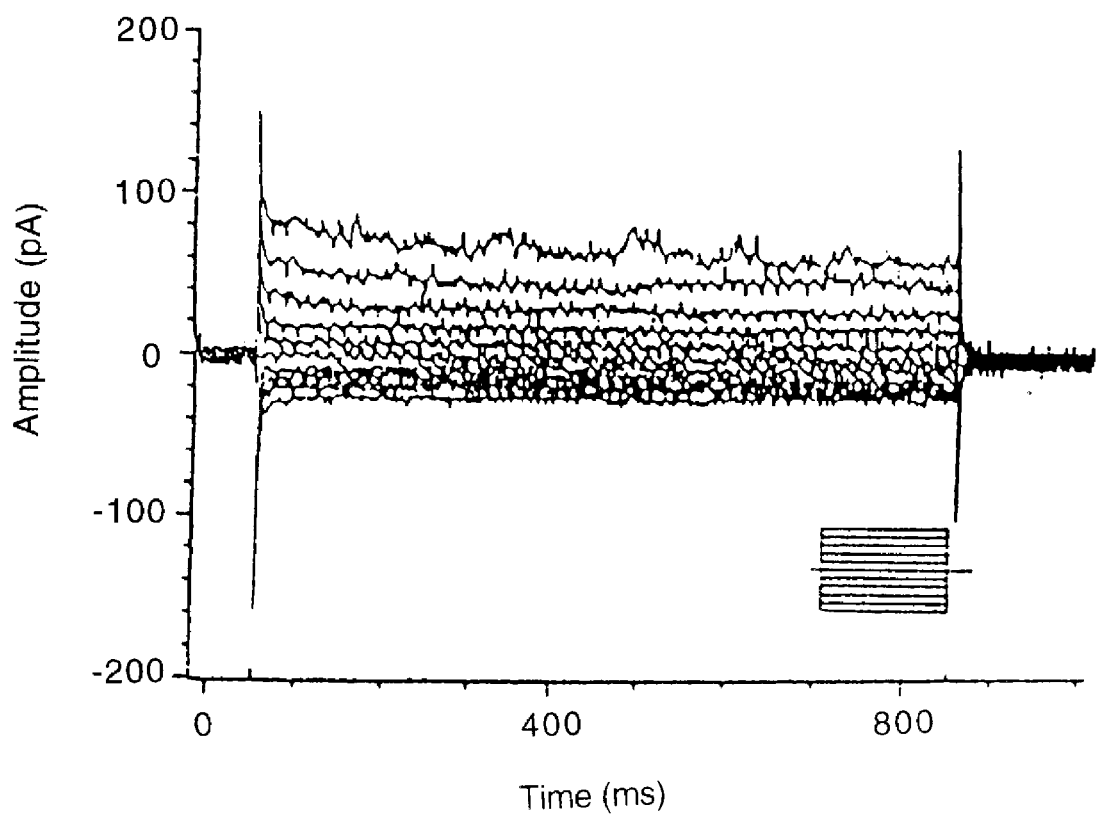
FIG. 7A shows the basal chloride currents showing outward rectification.
Figure 7B:
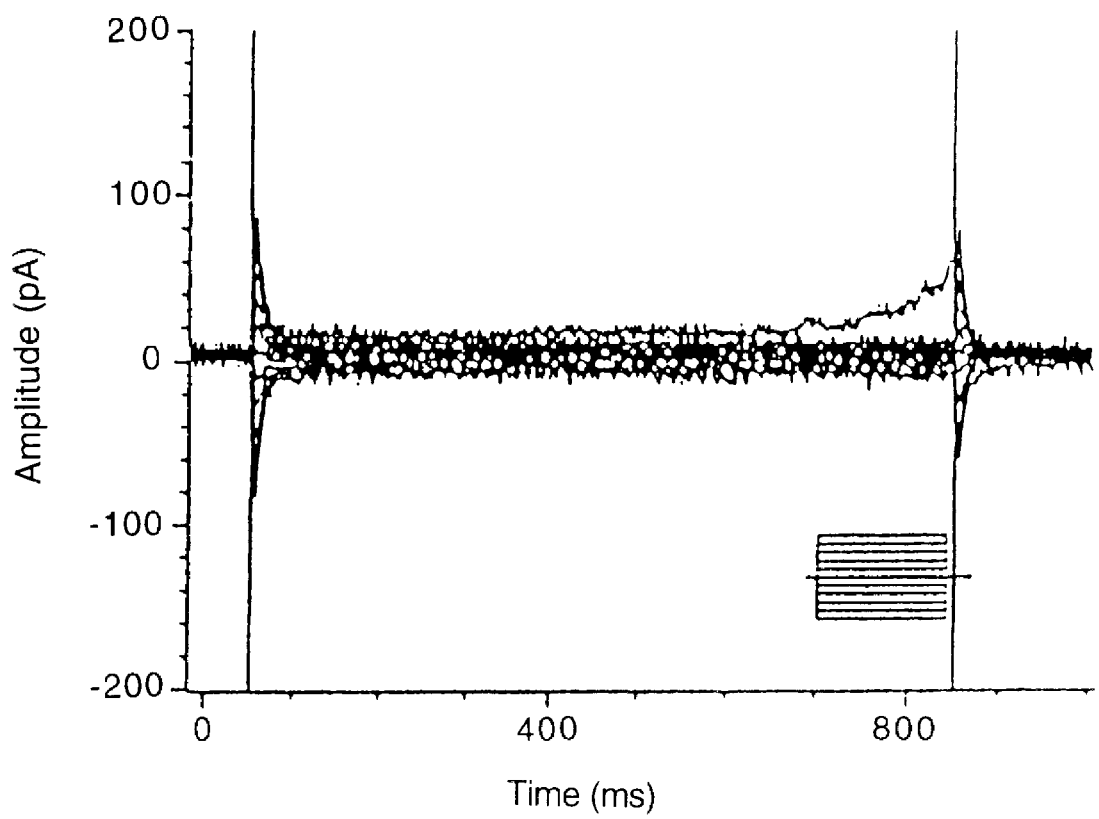
FIG. 7B shows chloride currents in the same cell following 100 mM DIDS treatment.

Cells are cultured with sub-inhibitory concentrations of aminoglycosides and assayed for the appearance of CFTR function. If the appearance of a cAMP-stimulated halide permeability (above that in the control cells) is demonstrated with the SPQ assay following aminoglycoside treatment, it would indicate that a functionally significant level of full-length, functional CFTR had been produced. Cells that have not been exposed to aminoglycosides are used as negative controls to confirm that the induced activity is dependent upon the suppression of the premature stop mutation. Whole cell recordings of IB3-1 cells are also performed before and after exposure to aminoglycosides providing more sensitive and quantitative measurement of any changes in chloride conductance, and allowing determination of ion selectivity and the rectification of currents induced by cAMP activation following aminoglycoside treatment. Given the recent evidence suggesting that one aspect of CFTR's function is to stimulate the ORCC (Schwiebert et al., 1995), it is possible that the chloride current observed will exhibit outward rectification. If this is the case, DIDS (a blocker that inhibits the ORCC but not CFTR) is used to directly detect CFTR currents induced by cAMP activation following aminoglycoside treatment. High resistance seals can be obtained in IB3-1 cells following G-418 treatment. Furthermore, under depolarizing conditions outwardly rectified, DIDS-sensitive chloride currents in these cells (FIG. 7) can be seen. Thus, IB3-1 cell line are used to demonstrate that aminoglycoside treatment induces a cAMP-stimulated chloride conductance in cells carrying a CFTR premature stop mutation in the nuclear genome.

EXAMPLE 9
Suppression of premature stop mutations in a CFTR-G542X transgenic mouse A few years ago a transgenic mouse model was constructed in which the endogenous mouse CFTR gene had been disrupted, resulting in a CFTR (−/−) genotype (Snouwaert et al., 1992; Dorin et al., 1992; Ratcliff et al., 1993). These CFTR (−/−) animals exhibited limited lung pathology, but most (~95%) died due to intestinal blockage during the first month of life. Whitsett and co-workers also constructed a "bi-transgenic mouse" to demonstrate that the expression of human CFTR (hCFTR) could functionally correct the mouse knockout (Zhou et al., 1994). In this construct, the intestinal fatty acid binding protein (FABP) promoter was used to drive the gut-specific expression of hCFTR in the North Carolina CFTR (−/−) mouse, which completely lacks CFTR activity. The expression of wild type hCFTR significantly increased the survival of these animals. In addition, hCFTR expression provided a functional correction of ileal goblet cell and crypt cell hyperplasia and cAMP-stimulated chloride secretion. Interestingly, it was recently shown using a series of CF mice carrying different combinations of mutant CFTR alleles that a very low level of CFTR (~5% of wild type levels) was only partially capable of correcting the cAMP mediated chloride conductance, but caused a significant increase in the viability of these animals (Dorin et al., 1995). These results suggest that the correction of this gut-specific defect may provide a sensitive indication of an increase in functional CFTR expression. Most currently available CFTR null transgenic mice (including the North Carolina mouse) were constructed using a neomycin resistance cassette as the selectable marker. Animals constructed with this marker should retain the capacity to inactivate various aminoglycosides, include G-418. Recently, ΔF508 mice have been constructed that do not carry a neomycin resistance gene (Colledge et al., 1995). A ΔF508 mouse line is obtained through Jackson Labs, and these are crossed with mice expressing high levels of hCFTR-G542X mRNA (the level of expression is determined by RT-PCR analysis). Progeny heterozygous at both loci (hCFTR-G542X$^{+/-}$, ΔF508/$^{+}$) is identified by Southern blot analysis, and these heterozygous animals are bred to produce the desired ΔF508/ΔF508 mice expressing the hCFTR-G542X transgene.

The hCFTR-G542X$^{+/-}$, ΔF508/ΔF508 mice (along with ΔF508/ΔF508 controls lacking the hCFTR-G542X transgene) are used to test for aminoglycoside-mediated readthrough. Identical groups of each genotype are treated with or without G-418 (see TABLE 2).

G-418 is highly related structurally to gentamicin. Since the recommended dosage of gentamicin (used to treat bacterial infections) in mice is 5 mgm gentamicin (in the drinking water) per gram body weight per day, a G-418 treatment regimen is used using this dosage roughly 1 week after birth. Initially, a small volume of the aminoglycoside solution (~50 ml) containing 2.5 mgm of G-418 is delivered to the pups orally twice daily. The pups are kept with their mother and allowed to nurse normally. This protocol is continued until the animal either dies from intestinal blockage (which occurs ~95% of the time with ΔF508/ΔF508 mice by 30–40 days after birth) or successfully passes through this window of vulnerability. A statistically significant increase in the survival uency of the CFTR-G542X mice, but not the controls lacking the G542X transgene, indicates that the synthesis of full length, functional CFTR had been induced by aminoglycoside treatment.

TABLE 2

Groups for aminoglycoside suppression in mice carrying the hCFTR-G542X transgene

| Group | Genotype | | Aminoglycoside |
|---|---|---|---|
| 1 | ΔF508/ΔF508 | | − |
| 2 | ΔF508/ΔF508 | | + |
| 3 | ΔF508/ΔF508 | hCFTR-G542X | − |
| 4 | ΔF508/ΔF508 | hCFTR-G542X | + |

To confirm that readthrough is induced upon inoglycoside treatment, mice from treated and untreated groups are examined for both gross anatomical and histopathological changes to quantify whether a reduction of the pathology associated with the ΔF508/ΔF508 mice is observed following aminoglycoside treatment. ΔF508/ΔF508 controls lacking the hCFTR-G542X transgene (with and without drug treatment) are also included to confirm that any changes observed require: 1) the transgene; and 2) aminoglycoside treatment.

As described in the discussion on mRNA stability, it is possible that readthrough of the G542X stop mutation may be accompanied by an increase in the steady-state level of CFTR mRNA. To examine this possibility, one determines whether aminoglycoside treatment causes an increase in the steady-state level of the hCFTR- G542X mRNA by RT-PCR. Human CFTR-specific primers that are complementary to the mRNA distal to the nonsense codon are used to quantitate the hCFTR mRNA in animals from each experimental group. If an increase in the steady-state level of mRNA can be detected, it would suggest that the suppression of the G542X stop mutation by aminoglycoside treatment increases the stability of the mRNA expressed from the hCFTR-G542X. Finally, electrophysiological studies are carried out on mice from each study group to determine whether any improvement observed in the survival rate of the mice carrying the transgene corresponds to an electrophysiological correction of the chloride transport defect previously shown to be associated with the loss of CFTR in these animals (Clarke et al., 1992). This analysis includes short-circuit current measurements in freshly excised tissue from the intestine to determine whether aminoglycoside treatment results in the appearance of a cAMP-stimulated chloride current. Such a result would indicate that the expression of functional CFTR was induced by aminoglycoside treatment.

EXAMPLE 10
Characterizing The Molecular Mechanism Of Aminoglycoside-Mediated Suppression Of Premature Stop Mutations Previous results have suggested that aminoglycoside antibiotics alter the fidelity of translation by binding directly to the ribosome at one or more sites. However, most of those studies directed toward understanding the mechanism of aminoglycoside10 induced ambiguity during translation were directed toward the misreading of sense codons, rather than the suppression of stop codons (Davies et al., 1965; Gorini, 1974). Furthermore, the effect of sequence context on the suppression of stop codons by different aminoglycosides was not characterized. The present invention demonstrates that the suppression of stop codons by some aminoglycosides (such as hygromycin B) is context specific, while the suppression by others (such as G-418 and gentamicin) is largely insensitive to the surrounding context.

The data on the suppression of stop mutations are consistent with the hypothesis that eukaryotic polypeptide chain release factor (eRF) binds a termination sequence in the mRNA that includes both the termination codon in the ribosomal A site and a limited number of surrounding nucleotides. Once bound, the eRF would mediate the hydrolysis of the ester bond between the polypeptide chain and the final tRNA located in the ribosomal P site, thus releasing the nascent polypeptide chain. Both a sub-optimal sequence context surrounding the stop codon and the presence of (at least some) aminoglycosides appear to interfere with eRF binding or function. This model predicts that the effect of aminogycosides on translation termination should be dependent upon the source of the eRF present in the termination reaction. Yeast and human cells exhibit differences in the effect of certain aminoglycosides on readthrough. This suggests that the yeast and human eRFs may also respond differently to changes in either sequence context or to aminoglycoside challenge.

Rabbit polyclonal antibodies to the eRF1and eRF3 proteins are prepared from both yeast and humans. To do this, each is expressed as a fusion protein with the E. coli TrpE protein (Koerner et al., 1991). TrpE fusion proteins are quite useful as immunogens. TrpE fusions overproduced in E. coli are usually found in inclusion bodies, which greatly simplify their purification. The overexpressed fusion proteins are solubilized from the inclusion bodies and further purified by ion exchange chromatography using a BioRad Biologic system (if needed). The fusion proteins are resolved by SDS-PAGE and excised from the gel. This approach is use to overproduce and purify proteins expressed in E. coli with excellent results. Antibodies are raised in rabbits by standard immunization protocols and sera screened by immunoprecipitation and western blot analysis.

EXAMPLE 11

Determining the effects of sequence context and aminoglycosides on a well-defined set of extended termination signals in human cells Using a sensitive yeast readthrough assay system to determine how the local sequence context influences the efficiency of translation termination in yeast, it was found that the local sequence context can alter the efficiency of translation termination by as much as 250 fold. While little is currently known about the role of sequence context on the efficiency of translation termination in human cells, limited evidence suggests that the local sequence context also plays a role in determining the efficiency of translation termination. As previously shown for E. coli and yeast, the first nucleotide following the stop codon (and possibly more distal nucleotides) appears to be important in determining the efficiency of translation termination in human cells (McCaughan et al., 1995).

A series of matched readthrough constructs (Fearon et al., 1994; Bonetti et al., 1995) are adapted to determine the importance of sequence context on translation termination in human cells. To do this, one PCR amplifies the "readthrough regions" of the constructs (the stop codon and surrounding context) using primers that introduce a unique restriction site upstream of the readthrough regions. Each fragment is then cloned into a vaccinia-T7 β-galactosidase expression vector and sequenced to ensure that no additional mutations were introduced. HeLa cells are infected with these vaccinia-T7 β-galactosidase viruses containing either control or nonsense codons surrounded by different readthrough contexts. At designated times after infection, parallel sets of infected cells are used to measure the β-galactosidase protein level (by enzymatic assay) and the β-galactosidase mRNA level (by northern analysis). From these values one can calculate the amount of β-galactosidase expressed per unit amount of mRNA as previously described (Bonetti et al., 1995) to accurately determine the level of readthrough that occurs with each construct.

Some aminoglycosides can influence readthrough in different ways as a function of the local sequence context. To identify those aminoglycosides capable of suppressing the broadest spectrum of disease-causing premature stop codons, one needs to identify compounds that: 1) can accumulate in human cells at concentrations sufficiently high to promote readthrough (without toxicity), and 2) and can stimulate readthrough at premature stop codons in the broadest range of sequence contexts. The vaccinia-βgalactosidase readthrough system is used to systematically examine the ability of various aminoglycosides to induce the suppression of premature stop codons in various contexts. Each drug is examined in a range of concentrations to determine the maximum level of readthrough that can be induced without toxicity.

EXAMPLE 12

Clinical trials to show the efficacy of aminoglycoside-mediated suppression of premature stop mutations in the lung epithelia of CF patients Initial trials are straightforward since clinically relevant aminoglycosides such as gentamicin induce supression. First, one determines whether gentamicin induces CFTR function in the nasal epithelia of patients with premature stop mutations, but not homozygous ΔF508 controls. This effect could be monitored by nasal potential difference measurements in these patients. It is clear that aminoglycosides can enter human cells and influence the fidelity of translation in a manner similar to that previously described in E. cole (Davies et al., 1965; Gorini, 1974). The permeability of these compounds into human cells is simply lower, which allows them to be used so effectively as antibacterial agents. Although nephrotoxicity and ototoxicity are common side effects of the systemic use of aminoglycosides due to their higher permeability in these organs, a recent study indicated that the aerosilization of tobramycin three times a day into the lungs of CF patients over several months did not result in these side effects (Ramsey et al., 1993). This indicates that this route of administration does not allow toxic levels of the drug to enter the bloodstream, and suggests that the regular administration of an aminoglycoside into the lung of CF patients to suppress premature stop mutations may also be feasible.

The suppression of stop mutations in the treatment of other diseases is also evaluated. For example, a recent compilation of 178 examples of premature stop mutations that cause human disease was recently reported (Atkinson and Martin, 1994). Among these, 25 distinct premature stop mutations in the P53 gene alone were reported to be responsible for various types of cancer. Thus, while cystic fibrosis provides an ideal model system to explore the use of aminoglycoside-based therapy to suppress premature stop mutations, this approach may ultimately become an important tool in the treatment of many other diseases as well.

The following references were cited herein:
1. Atkinson, et al., *Nucleic Acids Research* 22, 1327–1334, (1994)
2. Ayer, D., et al., *Science* 231, 393–395 (1986).
3. Bedwell, et al., *Ped. Pulm. Supplement* 12, 232, (1995).
4. Belgrader, et al., *Proc. Natl. Acad. Sci. USA* 90, 482–486, (1993).
5. Berkower, et al., *EMBO J.* 10, 3777–3785, (1991).
6. Bonetti, et al., *J. Mol. Biol.* 251, 334–345, (1995).
7. Bossi, L. *J. Mol. Biol.* 164, 73–87, (1983).
8. Bossi, L., Roth, J. R., *Nature* (London) 286, 123–127, (1980).

9. Brown, A. J. P., *Trends Cell Biol.* 3, 180–183, (1993).
10. Brown, et al., *Nucl. Acids Res.* 21, 3119–3123, (1993).
11. Brown, et al., *Nucl. Acids Res.* 18, 6339–6345, (1990).
12. Buckingham, et al., *Biochim. Biophys. Acta.* 1050, 259–262, (1990).
13. Clark, et al., *Science* 257, 1125–1128, (1992).
14. Colledge, et al., *Nat. Genet.* 10, 445–452, (1995).
15. Copeland, et al., *Ped. Pulm. Supplement* 12, 182, (1995).
16. Cuppens, et al., *J. Med. Genet.* 27, 717–719, (1990).
17. Cutting, G. R., 25, 7–10, (1993).
18. Cutting, et al., *New Eng. J. Med.* 323, 1685–1689, (1990a).
19. Cutting, et al., *Nature* (London) 346, 366–369, (1990b).
20. Cystic Fibrosis Genetic Analysis Consortium, *Hum. Mut.* 4, 167–177, (1994).
21. Davies, et al., *Mol. Pharmacol.* 1, 93–106, (1965).
22. Dorin, et al., *Nature* 359, 211–215, (1992).
23. Dorin, et al., *Ped. Pulm. Supplement* 12, 231, (1995).
24. Eggertsson, et al., *Microbiol. Rev.* 52, 354–374, 1988.
25. Engelberg-Kulka, H., *Nucl. Acids Res.* 9, 983–991, (1981).
26. Eustice, et al., *J. Mol. Biol.* 188, 207–214, (1986).
27. Fearon, et al., *J. Biol. Chem.* 269, 17802–17808, (1994).
28. Feinstein, S. I., et al., *J. Mol. Biol.* 112, 453–470, (1977).
29. Feng, et al., *Proc. Natl. Acad. Sci. USA* 87, 8860–8863, (1990).
30. Feng, Y-X., et al., *J. Virol.* 63, 2870–2873, (1989).
31. Feng, et al., *J. Virol.* 66, 5127–5132, (1992).
32. Frolova, et al., *Nature* 372, 701–703, (1994).
33. Frolova, et al., *EMBO J.* 12, 4013–4019, (1993).
34. Fuerst, et al., (1986) *Proc. Natl. Acad. Sci. USA* 83, 8122–8126.
35. Gasparini, et al., *J. Med. Genet.* 29, 558–562, (1992).
36. Geitz, R. D., et al., *Gene* 74: 527–534, (1988).
37. Gesteland, et al., *Science* 257, 1640–1641, (1992).
38. Gorini, L., Streptomicin and misreading of the genetic code. In *Ribosomes*, M. Nomura, et al., Eds. Cold Spring Harbor Laboratory, Cold Spring Harbor, N.Y. 791–803, (1974).
39. Grenett, et al., 45. *Gene* 110, 239–243, (1992).
40. Hamosh, et al., *Hum. Mol. Genet.* 1, 542–544, (1992).
41. Hamosh, et al., *J. Clin. Invest.* 88, 1880–1885, (1991).
42. Hatfield, et al., *Crit. Rev. in Biochem. and Mol. Biol.* 25, 71–96, (1990).
43. Himmelfarb, et al., *Mol. and Cell. Bio.* 5, 816–822, (1985).
44. Hoshino, et al., *EMBO Journal* 8, 3807–3814, (1989).
45. Kerem, et al., *Proc. Natl. Acad. Sci. USA* 87, 8447–8451, (1990).
46. Koerner et al., [33] *Methods in Enzymology* 194, 477–490, (1991).
47. Kopczynski, et al., *Mol. Gen. Genet.* 234, 369–378, (1992).
48. Kopelowitz, et al., *J. Mol. Biol.* 225, 261–269, (1992).
49. Lee, et al., *Proc. Natl. Acad. Sci. USA* 87, 3508–3512, (1990).
50. Maquat, L.E., *RNA* 1, 453–465, (1995).
51. Martin, et al., *Mol. Gen. Genet.* 217, 411–418, (1989).
52. McCaughan, et al., *Proc. Natl. Acad. Sci.* 92, 5431–5435, (1995).
53. Miller, J., *J. Mol. Biol.* 164, 59–71, (1983).
54. Moffat, et al., *J. Bacteriol.* 176, 7115–7117, (1994).
55. Mottagui-Tabar, et al., *EMBO J.* 13: 249–257, (1994).
56. Palmer, et al., *Nature* 277, 148–150, (1979).
57. Pedersen, W. T., et al., *J. Mol. Biol.* 219, 231–241, (1991).
58. Pelham, H., *Nature* (London), 272, 469–471, (1978).
59. Poole, et al., *EMBO J.* 14, 151–158, (1995).
60. Ramsey, et al., *New. Eng. J. Med.* 328, 1740–1746, (1993).
61. Ratcliff, et al., *Nat. Genet.* 4, 35–41, (1993).
62. Schwiebert et al., *Cell* 81, 1063–1073, (1995).
63. Schwiebert, et al., *Am. J. Physiol.* 266, C1464–1477, (1994).
64. Sheppard, et al., *Cell* 76, 1091–1098, (1994).
65. Sherman, F., Suppression in the yeast Saccharomyces cerevisiae, In *The Molecular Biology of the Yeast Saccharomyces: Metabolism and Gene Expression*, J. N. Strathern, et al., Eds. Cold Spring Harbor Laboratory Press, Cold Spring Harbor, N.Y., 463–486, (1982).
66. Shoshani, et al., *Am. J. Hum. Genet.* 50, 222–228, (1992).
67. Singh, et al., *Nature* 277, 146–148, (1979).
68. Skuzeski, et al., *J. Mol. Biol.* 218, 365–373, (1991).
69. Snouwaert, et al., *Science* 257, 1083–1088, (1992).
70. Stansfield, et al., *EMBO J.* 14, 4365–4373, (1995).
71. Strong, et al., *Hum. Mol. Genet.* 2, 225–230, (1993).
72. Timchenko, L., et al., *Proc. Natl. Acad. Sci. USA* 91, 2777–2780, (1994).
73. Urlaub, et al., *Mol. Cell Biol.* 9: 2868–2880, (1989).
74. Waity, et al., Antimicro. Agents & Chemo. 6:579–581, (1974).
75. Wills, et al., *Proc. Natl. Acad. Sci. USA* 88, 6991–6995, (1991).
76. Wilson, P. G., et al., *J. Mol. Biol.* 199, 559–573, (1988).
77. Yarus, M., et al., Precision of protein biosynthesis, In *Gene Function in Prokaryotes.* J. Beckwith, J. Davies, and J. Gallant, Eds. Cold Spring Harbor Laboratory Press, Cold Spring Harbor, N.Y. 23–63, (1984).
78. Yoshinaka, et al., *Proc. Natl. Acad. Sci.* 82, 1618–1622, (1985).
79. Zeitlin, et al., *Am. J. Respir. Cell Mol. Biol.* 4, 313–319, (1991).
80. Zhou, et al., *Science* 266, 1705–1708, (1994).
81. Zhouravleva, et al., *EMBO J.* 14, 4065–4072, (1995).
82. Zubay, G., *Annu. Rev. Genet.* 7, 267–287, (1973).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of stimulating expression of a functional full-length cystic fibrosis transmembrane conductance regulator protein in an individual in need of such treatment, comprising the step of administering to said individual a pharmacologically effective dose of an aminoglycoside.

2. The method of claim 1, wherein said individual has cystic fibrosis.

3. The method of claim 1, wherein said individual has a premature stop mutation selected from the group consisting of G542X, R553X, R1162X, and W1282X.

4. The method of claim 1, wherein said aminoglycoside is selected from the group consisting of gentamicin, G418, hygromycin B, paromomycin, tobramycin, and lividomycin A.

5. The method of claim 1, wherein said gentamicin is administered in a dose of from about 1 mg/kg to about 500 mg/kg.

6. The method of claim 1, wherein said G418 is administered in a dose of from about 1 mg/kg to about 1000 mg/kg.

7. A method of treating cystic fibrosis in an individual in need of such treatment, comprising the step of administering to said individual a therapeutically effective dose of an aminoglycoside.

8. The method of claim 7, wherein said aminoglycoside is selected from the group consisting of gentamicin, G418, hygromycin B, paromomycin, tobramycin, and lividomycin A.

9. The method of claim 7, wherein said gentamicin is administered in a dose of from about 1 mg/kg to about 500 mg/kg.

10. The method of claim 7, wherein said G418 is administered in a dose of from about 1 mg/kg to about 1000 mg/kg.

11. The method of claim 7, wherein said aminoglycoside suppresses a premature stop mutation.

12. The method of claim 11, wherein said premature stop mutation is selected from the group consisting of G542X, R553X, R1162X, and W1282X.

* * * * *